United States Patent [19]

Raddatz et al.

[11] Patent Number: 4,950,648
[45] Date of Patent: Aug. 21, 1990

[54] ANALGESIC

[75] Inventors: Peter Raddatz, Darmstadt; Wolf-Dietrich Weber, Reinheim; Andrew Barber, Darmstadt; Hans-Peter Wolf, Alsbach-Hähnlein; Christoph Seyfried, Jugendheim, all of Fed. Rep. of Germany

[73] Assignee: Merck Patent Gesellschaft Mit Beschränkter Haftung, Darmstadt, Fed. Rep. of Germany

[21] Appl. No.: 271,463

[22] Filed: Nov. 15, 1988

[30] Foreign Application Priority Data

Nov. 16, 1987 [DE] Fed. Rep. of Germany ....... 3738844

[51] Int. Cl.$^5$ .................... A61K 31/50; A61K 31/505
[52] U.S. Cl. ..................................... 514/254; 514/258; 514/269
[58] Field of Search ......................... 514/269, 254, 258

[56] References Cited

U.S. PATENT DOCUMENTS 4,485,107 11/1984 Kennis et al. ....................... 514/269

FOREIGN PATENT DOCUMENTS 3601731 7/1987 Fed. Rep. of Germany .

Primary Examiner—Stanley J. Friedman
Attorney, Agent, or Firm—Millen, White & Zelano

[57] ABSTRACT

New analgesic compositions containing a compound of the formula I

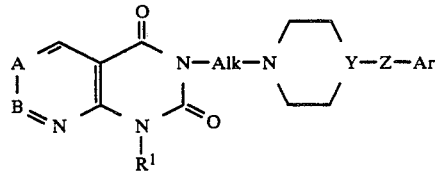

wherein
=A—B= is =CH—CH= or —N—CR$^2$=,
Alk is an alkylene group having 2–4 C atoms,
R$^1$ is H, dialkylaminoalkyl, carboxyalkyl, alkoxycarbonylalkyl, carbamoylalkyl, N-alkylcarbamoylalkyl or N,N-dialkylcarbamoylalkyl,
Y is CH or N,
Z is a bond or —CO—,
Ar is a phenyl, thienyl or pyridyl group which is unsubstituted or substituted one or more times by alkyl, alkoxy, F, Cl, Br, I and/or CF$_3$, and
R$^2$ is H, alkyl, alkoxy or alkylthio, in which the alkyl, alkoxy and alkylthio groups each contain 1–4 C atoms, and/or one of its physiologically acceptable salts.

19 Claims, No Drawings

ANALGESIC

BACKGROUND OF THE INVENTION

The invention relates to analgesic compositions, in particular, compositions which can be used as analgesics in human and veterinary medicine.

SUMMARY OF THE INVENTION

An object of the invention is to provide new analgesics with high efficacy, especially new analgesics which exhibit the undesired side-effects of the known analgesics either not at all or only to a small extent.

Upon further study of the specification and appended claims, further objects and advantages of this invention will become apparent to those skilled in the art.

These objects are achieved by providing analgesics containing a compound of the formula I and/or its physiologically acceptable salts:

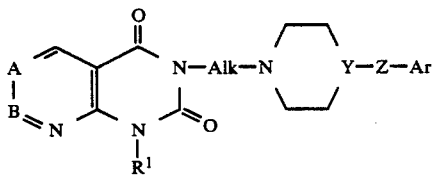

wherein
—A—B— is =CH—CH= or =N—CR$^2$=,
Alk is an alkylene group having 2-4 C atoms,
R$^1$ is H, dialkylaminoalkyl, carboxyalkyl, alkoxycarbonylalkyl, carbamoylalkyl, N-alkylcarbamoylalkyl or N,N-dialkylcarbamoylalkyl,
Y is CH OR N,
Z is a bond or —CO—,
Ar is a phenyl, thienyl or pyridyl group which is unsubstituted or substituted one or more times by alkyl, alkoxy, F, Cl, Br, I and/or CF$_3$, and
R$^2$ is H, alkyl, alkoxy or alkylthio,
in which the alkyl, alkoxy and alkylthio groups each contain 1-4 C atoms.

The compounds of the formula I and their salts are described in DE-A No. 3,601,731; however, there are no statements therein about an analgesic effect.

It has been found that the compounds of the formula I and their physiologically acceptable salts have analgesic properties; thus, the compounds have particularly potent effects in the writing test on mice or rats (for method, see Siegmund, Cadmus and Golu, Proc. Soc. Exp. Biol. 95, (1957), 729–731). The analgesic effect can also be detected in the tail-flick test on mice or rats (for methods see d'Amour and Smith, J. Pharmacol, Exp. Ther. 72, (1941), 74–79) and in the hotplate test (see Schmauss and Yaksh, J. Pharmacol. Exp. Ther. 228, (1984), 1–12 and the literature cited therein).

In the formula I the group =A—B= is preferably =C—CH= or =N—C(CH$_3$)=. Alk is preferably —CH$_2$—CH$_2$—; Alk can also be, preferably, —(CH$_2$)$_3$—, —(CH$_2$)$_4$—, —CH(CH$_3$)—, —CH(C$_2$H$_5$)—, —CH(CH$_3$)CH$_2$—, —CH$_2$CH(CH$_3$)—, —CH(CH$_3$)CH$_2$CH$_2$—, —CH$_2$CH(CH$_3$)CH$_2$—, —CH$_2$CH$_2$CH(CH$_3$)—, —CH(C$_2$H$_5$)CH$_2$—, —CH$_2$CH(C$_2$H$_5$)—, —CH(C$_3$H$_7$)— or —CH(iso—C$_3$H$_7$)—.

The alkyl groups are preferably methyl or ethyl, but are also propyl, isopropyl, butyl, sec.-butyl or tert.-butyl. Alkoxy is preferably methoxy or ethoxy, as well as propoxy, isopropoxy, butoxy, isobutoxy, sec.-butoxy or tert.-butoxy. Alkylthio is preferably methylthio or ethylthio, as well as propylthio, isopropylthio, butylthio, sec.-butylthio or tert.-butylthio.

Dialkylaminoalkyl is preferably 2-dimethylaminoethyl, 2-diethylaminoethyl, 2- or 3-dimethylaminopropyl or 2- or 3-diethylaminopropyl, as well as 2-, 3- or 4-dimethylaminobutyl, 2-, 3- or 4-diethylaminobutyl, 2-dipropylaminoethyl, 2-dibutylaminoethyl, 2- or 3-dipropylaminopropyl, 2- or 3-dibutylaminopropyl. Carboxylalkyl is preferably carboxymethyl, 1- or 2-carboxyethyl, as well as 1-, 2- or 3-carboxypropyl, 1-, 2-, 3- or 4-carboxybutyl. Alkoxycarbonylalkyl is preferably methoxycarbonylmethyl, ethoxycarbonylmethyl, 1- or 2-methoxycarbonylethyl, 1- or 2-ethoxycarbonylethyl, as well as propoxycarbonylmethyl, isopropoxycarbonylmethyl, butoxycarbonylmethyl, 1-, 2-or 3-methoxycarbonylpropyl, 1-, 2- or 3-ethoxycarbonylpropyl, 1-, 2-, 3- or 4-methoxycarbonylbutyl, 1-, 2-, 3-or 4-ethoxycarbonylbutyl. Carbamoylalkyl is preferably carbamoylmethyl, 1- or 2-carbamoylethyl, as well as 1-, 2- or 3-carbamoylpropyl, 1-, 2-, 3- or 4-carbamoylbutyl. N-alkylcarbamoylalkyl is preferably N-methylcarbamoylmethyl, N-ethylcarbamoylmethyl, 1- or 2-N-methylcarbamoylethyl, 1- or 2-N-ethylcarbamoylethyl, as well as N-propylcarbamoylmethyl, N-isopropylcarbamoylmethyl, N-butylcarbamoylmethyl, 1-, 2- or 3-N-methylcarbamoylpropyl, 1-, 2- or 3-N-ethylcarbamoylpropyl, 1-, 2-, 3- or 4-N-methylcarbamoylbutyl, 1-, 2-, 3- or 4-N-ethylcarbamoylbutyl. N,N-dialkylcarbamoylalkyl is preferably N,N-dimethylcarbamoylmethyl, N,N-diethylcarbamoylmethyl, 1- or 2-N,N-dimethylcarbamoylethyl, 1- or 2-N,N-diethylcarbamoylethyl, as well as N,N-dipropylcarbamoylmethyl, N,N-diisopropylcarbamoylmethyl, N,N-dibutylcarbamoylmethyl, 1-, 2- or 3-N,N-dimethylcarbamoylpropyl, 1-, 2-or 3-N,N-diethylcarbamoylpropyl, 1-, 2-, 3-or 4-N,N-dimethylcarbamoylbutyl, 1-, 2-, 3- or 4-N,N-diethylcarbamoylbutyl.

The group Y—Z— is preferably N— or CH—CO—, but also N—CO— or CH—.

Ar is preferably phenyl, o-, m- or p-tolyl, o-, m- or p-ethylphenyl, o-, m- or p-methoxyphenyl, o-, m- or p-ethoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, 2,3-, 2,4-, 2,5-, 2,6-, 3,4- or 3,5-dimethylphenyl, 2,3-, 2,4-, 2,5-, 2,6-, 3,4- or 3,5-dimethoxphenyl, 3,4,5-trimethoxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2- or 3-thienyl, 2-, 3- or 4-pyridyl.

Accordingly, particularly preferred compounds of the formula I are those in which at least one of the radicals has one of the abovementioned preferred meanings. Some preferred groups of compounds can be indicated by the following part-formulae Ia to In which correspond to the formula I and in which the unspecified radicals have the meaning mentioned for formula I but in which

| | | |
|---|---|---|
| in Ia | =A—B= | is =CH—CH=; |
| in Ib | =A—B= | is =N—CR$^2$=; |
| in Ic | =A—B= | is N—C(CH$_3$)=; |
| in Id | Alk | is —CH$_2$CH$_2$—; |
| in Ie | R$^1$ | is H; |
| in If | R$^1$ | is dialkylaminoalkyl, carboxyalkyl, alkoxycarbonylalkyl, carbamoylalkyl, N-alkylcarbamoylalkyl or N,N-dialkyl- |

-continued

| | | |
|---|---|---|
| in Ig | R¹ | carbamoylalkyl; is H, 2-dimethylaminoethyl, 3-diethylaminopropyl, carboxymethyl or ethoxycarbonylmethyl; |
| in Ih | Y—Z— | is N—; |
| in Ii | Y—Z— | is CH—CO—; |
| in Ij | Ar | is phenyl, tolyl, methoxyphenyl, fluorophenyl, chlorophenyl, trifluoromethylphenyl, dimethoxyphenyl, trimethoxyphenyl, dichlorophenyl or pyridyl; |
| in Ik | Ar | is o-methoxyphenyl; |
| in Il | =A—B= | is =CH—CH= or =N—C(CH₃)= |
| | R¹ | is H, dialkylaminoalkyl, carboxyalkyl or alkoxycarbonylalkyl, |
| | Y—Z— | is N— or CH—CO— and |
| | Ar | is phenyl, methoxyphenyl, fluorophenyl, trifluoromethylphenyl or pyridyl; |
| in Im | =A—B= | is =CH—CH= or =N—C(CH₃)=, |
| | R¹ | is H, dialkylaminoalkyl, carboxyalkyl or alkoxycarbonylalkyl, |
| | Y—Z— | is N— or CH—CO— and |
| | Ar | is methoxyphenyl, fluorophenyl or trifluoromethylphenyl; |
| in In | =A—B= | is =CH—CH= or =N—C(CH₃)=, |
| | R¹ | is H or dialkylaminoalkyl, |
| | Y—Z— | is N— or CH—CO— and |
| | Ar | is o-methoxyphenyl. |

In a particularly preferred individual compound, =A—B= is =CH—CH=, R¹ is H, Alk is —CH₂CH₂—, Y is CH, Z is CO and Ar is p-fluorophenyl.

Details of the preparation of the compounds of the formula I are described in DE-A No. 3,601,731.

Examples of suitable physiologically acceptable acid addition salts of the bases of the formula I are salts with inorganic acids, for example sulfuric acid, nitric acid, hydrohalic acids such as hydrochloric acid or hydrobromic acid, phosphoric acids such as orthophosphoric acid, sulfamic acid as well as with organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane-or ethanesulfonic acid, ethanedisulfonic acid, 2-hydroxyethanesulfonic acid, benzenesulfonic acid, p-toluenesulfonic acid, naphthalenemono- and-disulfonic acids, and lauryl sulfuric acid.

Conversely, an acid of the formula I (R¹-carboxyalkyl) can be converted into one of its metal or ammonium salts by treatment with a base. Particularly suitable salts are the sodium, potassium, magnesium, calcium and ammonium salts, as well as substituted ammonium salts.

In the preparation of the analgesics according to the invention, it is possible for the compounds of the formula I and/or their physiologically acceptable salts to be converted into a suitable administration form together with at least one solid, liquid and/or semiliquid vehicle or auxiliary and, where appropriate, in combination with one or more other active compounds.

The analgesics according to the invention can be used as pharmaceuticals in human or veterinary medicine. Suitable vehicles are organic or inorganic substances which are suitable for enteral (for example oral), parenteral or topical administration and which do not react with the new compounds, for example water, vegetable oils, benzyl alcohols, alkylene glycols, polyethylene glycols, glycerol triacetate, gelatine, carbohydrates such as lactose or starch, magnesium stearate, talc or vaseline. Particularly used for oral administration are tablets, pills, coated tablets, capsules, powders, granules, syrups, elixirs or drops, for rectal administration suppositories, for parenteral administration solutions, preferably oily or aqueous solutions, as well as suspensions, emulsions or implants, and for topical administration ointments, creams or powders. The new compounds can also be freeze-dried, and the resulting lyophilizates used, for example, for preparing products for injection. The formulations mentioned can be sterilized and/or contain auxiliaries such as lubricants, preservatives, stabilizers and/or wetting agents, emulsifiers, salts for influencing the osmotic pressure, buffer substances, pigments, flavorings and/or perfumes. They can, if desired, also contain one or more other active compounds, for example one or more vitamins.

The invention also relates to the use of the compounds of the formula I and/or their physiologically acceptable salts for controlling attacks of pain.

For this the substances are, as a rule, administered in analogy to known compounds having analgesic activity, such as ketanserin, ritanserin or guanethidine, preferably in doses between about 1 and 100 mg, in particular between 2 and 20 mg, per dose unit. The daily dose is preferably between about 0.02 and 2 mg/kg of body weight. The specific dose for each particular patient depends, however, on a wide variety of factors, for example on the efficacy of the specific compound used, on the age, body weight, general state of health, sex, on the diet, on the time and route of administration, on the rate of excretion, pharmaceutical combination and severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application(s) German P. No. 37 38 844.4, filed Nov. 16, 1987, are hereby incorporated by reference.

EXAMPLES

Preparation Example 1

A mixture of 2.06 g of ethyl 2-ethoxycarbonylaminonicotinate (m.p. 60°, obtainable by boiling ethyl 2-aminonicotinate with ethyl chloroformate for 5 h in the presence of N,N-diisopropylethylamine in toluene) and 2.54 g of 1-(2-aminoethyl)-4-p-fluorobenzoylpiperidine (Rf 0.43 on silica gel with butanol/ethanol/water/ethyl acetate/acetic acid 50:50:50:25:25) is heated at 190° for 1 h. The mixture is cooled and taken up in methanol and, on cooling, 3-[2-(4-p-fluorobenzoylpiperidino)ethyl]-2,4-dioxo-1,2,3,4-tetrahydropyrido[2,3-d]pyrimidine is obtained, m.p. 237°. Hydrochloride m.p. 297°–298°. Fumarate m.p. 253°–255°.

The following 2,4-dioxo-1,2,3,4-tetrahydropyrido[2,3-d]pyrimidines are obtained analogously with the corresponding 1-(2-aminoethyl)-4-Ar-piperazines or —4—ArCO— piperidines:
3-[2-(4-phenylpiperazino)-ethyl]-, hydrochloride, m.p. 317°-319°
3-[3-(4-phenylpiperazino)-propyl]-
3-[4-(4-phenylpiperazino)-butyl]-
3-[2-(4-o-tolylpiperazino)-ethyl]-
3-[2-(4-m-tolylpiperazino)-ethyl]-
3-[2-(4-p-tolylpiperazino)-ethyl]-
3-[2-(4-o-butylphenylpiperazino)-ethyl]-
3-[2-(4-o-methoxyphenylpiperazino)-ethyl]- m.p. 213°-215°; hydrochloride, m.p. 242°-245°
3-[2-(4-m-methoxyphenylpiperazino)-ethyl]-, m.p. 264°; hydrochloride, m.p. 270°-272°
3-[2-(4-p-methoxyphenylpiperazino)-ethyl]-, hydrochloride, m.p. 238°-240°
3-[2-(4-o-ethoxyphenylpiperazino)-ethyl]-
3-[2-(4-p-butoxyphenylpiperazino)-ethyl]-
3-[2-(4-(3,4-dimethoxyphenyl)-piperazino)-ethyl]-
3-[2-(4-(3,4,5-trimethoxyphenyl)-piperazino)-ethyl]-, fumarate, m.p. 229°-230°
3-[2-(4-o-fluorophenylpiperazino)-ethyl]-, hydrochloride, m.p. 312°-315°
3-[2-(4-m-fluorophenylpiperazino)-ethyl]-
3-[2-(4-p-fluorophenylpiperazino)-ethyl]-, m.p. 234°; dihydrochloride, m.p. 278°-279°
3-[2-(4-o-chlorophenylpiperazino)-ethyl]-
3-[2-(4-m-chlorophenylpiperazino)-ethyl]-
3-[2-(4-p-chlorophenylpiperazino)-ethyl]-
3-[2-(4-(3,4-dichlorophenyl)-piperazino)-ethyl]-, hydrochloride, m.p. 282°-286°
3-[2-(4-o-bromophenylpiperazino)-ethyl]-
3-[2-(4-m-bromophenylpiperazino)-ethyl]-
3-[2-(4-p-bromophenylpiperazino)-ethyl]-
3-[2-(4-o-trifluoromethylphenylpiperazino)-ethyl]-
3-[2-(4-m-trifluoromethylphenylpiperazino)-ethyl]-, m.p. 210°
3-[2-(4-p-trifluoromethylphenylpiperazino)-ethyl]-
3-[2-(4-(2-thienyl)-piperazino)-ethyl]-
3-[2-(4-(3-thienyl)-piperazino)-ethyl]-
3-[2-(4-(2-pyridyl)-piperazino)-ethyl]- m.p. 235°-238°; hydrochloride, m.p. 258°-262°
3-[2-(4-(3-pyridyl)-piperazino)-ethyl]-
3-[2-(4-(4-pyridyl)-piperazino)-ethyl]-
3-[2-(4-benzoylpiperidino)-ethyl]-
3-[3-(4-benzoylpiperidino)-propyl]-
3-[4-(4-benzoylpiperidino)-butyl]-
3-[2-(4-o-toluylpiperidino)-ethyl]-
3-[2-(4-m-toluylpiperidino)-ethyl]-
3-[2-(4-p-toluylpiperidino)-ethyl]-
3-[2-(4-o-anisoylpiperidino)-ethyl]-, m.p. 183°-186°
3-[2-(4-m-anisoylpiperidino)-ethyl]-
3-[2-(4-p-anisoylpiperidino)-ethyl]-
3-[2-(4-o-fluorobenzoylpiperidino)-ethyl]-
3-[2-(4-m-fluorobenzoylpiperidino)-ethyl]-
3-[2-(4-o-chlorobenzoylpiperidino)-ethyl]-
3-[2-(4-m-chlorobenzoylpiperidino)-ethyl]-
3-[2-(4-p-chlorobenzoylpiperidino)-ethyl]-
3-[2-(4-o-bromobenzoylpiperidino)-ethyl]-
3-[2-(4-m-bromobenzoylpiperidino)-ethyl]-
3-[2-(4-p-bromobenzoylpiperidino)-ethyl]-
3-[2-(4-o-trifluoromethylbenzoylpiperidino)-ethyl]-
3-[2-(4-m-trifluoromethylbenzoylpiperidino)-ethyl]-, m.p. 213°-215°
3-[2-(4-p-trifluoromethylbenzoylpiperidino)-ethyl]-
3-[2-(4-(2-thenoyl)-piperidino)-ethyl]-
3-[2-(4-(3-thenoyl)-piperidino)-ethyl]-
3-[2-(4-picolinoyl-piperidino)-ethyl]-
3-[2-(4-nicotinoyl-piperidino)-ethyl]-
3-[2-(4-isonicotinoyl-piperidino)-ethyl]-.

The following 7-methyl-2,4-dioxo-1,2,3,4-tetrahydropyrimido[4,5-d]pyrimidines are obtained analogously with 5-ethoxycarbonyl-4-ethoxycarbonylamino-2-methylpyrimidine (obtainable from ethyl 4-amino-2-methylpyrimidine-5-carboxylate):
3-[2-(4-phenylpiperazino)-ethyl]-
3-[3-(4-phenylpiperazino)-propyl]-
3-[4-(4-phenylpiperazino)-butyl]-
3-[2-(4-o-tolylpiperazino)-ethyl]-
3-[2-(4-m-tolylpiperazino)-ethyl]-
3-[2-(4-p-tolylpiperazino)-ethyl]
3-[2-(4-o-methoxyphenylpiperazino)-ethyl]-, hemifumarate, m.p. 183°-186°
3-[2-(4-m-methoxyphenylpiperazino)-ethyl]-
3-[2-(4-p-methoxyphenylpiperazino)-ethyl]-
3-[2-(4-o-fluorophenylpiperazino)-ethyl]- hydrochloride, m.p. 290°-292°
3-[2-(4-m-fluorophenylpiperazino)-ethyl]-
3-[2-(4-p-fluorophenylpiperazino)-ethyl]-, fumarate, m.p. 237°
3-[2-(4-o-chlorophenylpiperazino)-ethyl]-
3-[2-(4-m-chlorophenylpiperazino)-ethyl]-
3-[2-(4-p-chlorophenylpiperazino)-ethyl]-
3-[2-(4-o-bromophenylpiperazino)-ethyl]-
3-[2-(4-m-bromophenylpiperazino)-ethyl]-
3-[2-(4-p-bromophenylpiperazino)-ethyl]-
3-[2-(4-o-trifluoromethylphenylpiperazino)-ethyl]-
3-[2-(4-m-trifluoromethylphenylpiperazino)-ethyl]-, m.p. 210°
3-[2-(4-p-trifluoromethylphenylpiperazino)-ethyl]-
3-[2-(4-(2-thienyl)-piperazino)-ethyl]-
3-[2-(4-(3-thienyl)-piperazino)-ethyl]-
3-[2-(4-(2-pyridyl)-piperazino)-ethyl]-
3-[2-(4-(3-pyridyl)-piperazino)-ethyl]-
3-[2-(4-(4-pyridyl)-piperazino)-ethyl]-
3-[2-(4-benzoylpiperidino)-ethyl]-
3-[3-(4-benzoylpiperidino)-propyl]-
3-[4-(4-benzoylpiperidino)-butyl]-
3-[2-(4-o-toluylpiperidino)-ethyl]-
3-[2-(4-m-toluylpiperidino)-ethyl]-
3-[2-(4-p-toluylpiperidino)-ethyl]-
3-[2-(4-o-anisoylpiperidino)-ethyl]-
3-[2-(4-m-anisoylpiperidino)-ethyl]-
3-[2-(4-p-anisoylpiperidino)-ethyl]-
3-[2-(4-o-fluorobenzoylpiperidino)-ethyl]-
3-[2-(4-m-fluorobenzoylpiperidino)-ethyl]-
3-[2-(4-p-fluorobenzoylpiperidino)-ethyl]-
3-[2-(4-o-chlorobenzoylpiperidino)-ethyl]-
3-[2-(4-m-chlorobenzoylpiperidino)-ethyl]-
3-[2-(4-p-chlorobenzoylpiperidino)-ethyl]-
3-[2-(4-o-bromobenzoylpiperidino)-ethyl]-
3-[2-(4-m-bromobenzoylpiperidino)-ethyl]-
3-[2-(4-p-bromobenzoylpiperidino)-ethyl]-
3-[2-(4-o-trifluoromethylbenzoylpiperidino)-ethyl]-
3-[2-(4-m-trifluoromethylbenzoylpiperidino)-ethyl]-
3-[2-(4-p-trifluoromethylbenzoylpiperidino)-ethyl]-
3-[2-(4-(2-thenoyl)-piperidino)-ethyl]-
3-[2-(4-(3-thenoyl)-piperidino)-ethyl]-
3-[2-(4-picolinoylpiperidino)-ethyl]-
3-[2-(4-nicotinoylpiperidino)-ethyl]-
3-[2-(4-isonicotinoylpiperidino)-ethyl]-.

Preparation Example 2

3.81 g of 3-[2-(4-o-methoxyphenylpiperazino)-ethyl]-2,4-dioxo-1,2,3,4-tetrahydropyrido[2,3-d]pyridine are dissolved in 160 ml of DMF, and 4.2 g of K$_2$CO$_3$ and 1.86 g of N-(3-chloropropyl)-N,N-diethylammonium chloride are added, and the mixture is stirred at 70° for 4 h. It is evaporated, water and dichloromethane are added, the pH is adjusted to 10, the phases are separated, and the organic phase is dried over sodium sulfate, filtered, evaporated and results in 1-(3-diethylaminopropyl)-3-[2-(4-o-methoxyphenylpiperazino)-ethyl]-2,4-dioxo-1,2,3,4-tetrahydropyrido[2,3-d]pyrimidine. Difumarate, m.p. 190°-192°.

The following 3-[2-(4-o-methoxyphenylpiperazino)-ethyl]-2,4-dioxo-1,2,3,4-tetrahydropyrido[2,3-d]pyrimidines are obtained analogously:
1-(2-dimethylaminoethyl)-, fumarate, m.p. 115°-117°
1-(2-diethylaminoethyl)-
1-(3-dimethylaminopropyl)-
1-(4-dimethylaminobutyl)-
1-carboxymethyl-, m.p. 215°-220°
1-(2-carboxyethyl)-
1-methoxycarbonylmethyl-,
1-ethoxycarbonylmethyl-, fumarate, m.p. 102°-105°
1-carbamoylmethyl-
1-(2-carbamoylethyl)-
1-N-methylcarbamoylmethyl-
1-N-ethylcarbamoylmethyl-
1-N,N-dimethylcarbamoylmethyl-
1-N,N-diethylcarbamoylmethyl-.

The examples which follow relate to pharmaceutical preparations which contain amines of the formula I or their acid addition salts:

Example A: Tablets

A mixture of 1 kg of 3-[2-(4-o-methoxyphenylpiperazino)-ethyl]-7-methyl-2,4-dioxo-1,2,3,4-tetrahydropyrimido[4,5-d]pyrimidine, 4 kg of lactose, 1.2 kg of potato starch, 0.2 kg of talc and 0.1 kg of magnesium stearate is compressed to tablets in a customary manner and in such a way that each tablet contains 10 mg of active compound.

Example B: Coated tablets

Tablets are compressed in analogy to Example A and are then coated in a customary manner with a coating composed of sucrose, potato starch, talc, tragacanth and pigment.

Example C: Capsules 2 kg of 3-[2-(4-p-fluorobenzoylpiperidino)-ethyl]-2,4-dioxo-1,2,3,4-tetrahydropyrimido[4,5-d]pyrimidine hydrochloride are dispensed into hard gelatine capsules in a customary manner and in such a way that each capsule contains 20 mg of active compound.

Example D: Ampoules

A solution of 1 kg of 1-(3-diethylaminopropyl)-3-[2-(4-o-methoxyphenylpiperazino)-ethyl]-2,4-dioxo-1,2,3,4-tetrahydropyrido[2,3-d]pyridine difumarate in 30 liters of double-distilled water is filtered sterile, dispensed into ampoules, freeze-dried under sterile conditions and sealed sterile. Each ampoule contains 2 mg of active compound.

Tablets, coated tablets, capsules and ampoules which contain one or more of the other active compounds of the formula I and/or their physiologically acceptable acid addition salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of controlling pain in a patient comprising administering to said patient an effective amount of a pyrimidine derivative of the formula wherein
=A—B= is =CH—CH= or =N—CR$^2$=;
Alk is an alkylene group having 2–4 C atoms;
R$^1$ is H, dialkylaminoalkyl, carboxylalkyl, alkoxycarbonylalkyl, carbamoylalkyl, N-alkylcarbamoylalkyl or N,N-dialkylcarbamoylalkyl;
Y is CH or N;
Z is a bond or —CO—;
Ar is a phenyl, thienyl or pyridyl group which is unsubstituted or substituted one or more times by alkyl, alkoxy, F, Cl, Br, I and/or CF$_3$, and
R$^2$ is H, alkyl, alkoxy or alkylthio;
in which the alkyl, alkoxy and alkylthio groups each contain 1–4 C atoms, and/or one of its physiologically acceptable salts.

2. A method according to claim 1, wherein =A—B= is =CH—CH=.

3. A method according to claim 1, wherein =A—B= is =N—CR$^2$=.

4. A method according to claim 1, wherein =A—B= is N—C(CH$_3$)=.

5. A method according to claim 1, wherein Alk is —CH$_2$CH$_2$—.

6. A method according to claim 1, wherein R$^1$ is H.

7. A method according to claim 1, wherein R$^1$ is dialkylaminoalkyl, carboxyalkyl, alkoxycarbonylalkyl, carbamoylalkyl, N-alkylcarbamoylalkyl or N,N-dialkylcarbamoylalkyl.

8. A method according to claim 1, wherein R$^1$ is H, 2-dimethylaminoethyl, 3-diethylaminopropyl, carboxymethyl or ethoxycarbonylmethyl.

9. A method according to claim 1, wherein Y—Z— is N—.

10. A method according to claim 1, wherein Y—Z— is CH—CO—.

11. A method according to claim 1, wherein Ar is phenyl, tolyl, methoxyphenyl, fluorophenyl, chlorophenyl, trifluoromethylphenyl, dimethoxyphenyl, trimethoxyphenyl, dichlorophenyl or pyridyl.

12. A method according to claim 1, wherein Ar is o-methoxyphenyl.

13. A method according to claim 1, wherein =A—B= is =CH—CH= or =N—C(CH$_3$)=;

$R^1$ is H, dialkylaminoalkyl, carboxyalkyl or alkoxycarbonylalkyl;
Y—Z— is N— or CH—CO—; and
Ar is phenyl, methoxyphenyl, fluorophenyl, trifluoromethylphenyl or pyridyl.

14. A method according to claim 1, wherein
=A—B= is =CH—CH= or =N—C(CH$_3$)=;
$R^1$ is H, dialkylaminoalkyl, carboxyalkyl or alkoxycarbonylalkyl;
Y—Z— is N— or CH—CO—; and
Ar is methoxyphenyl, fluorophenyl or trifluoromethylphenyl.

15. A method according to claim 1, wherein
=A—B= is =CH—CH= or =N—C(CH$_3$)=;
$R^1$ is H or dialkylaminoalkyl;
Y—Z— is N— or CH—CO—; and
Ar is o-methoxyphenyl.

16. A method according to claim 1, wherein
=A—B= is =CH—CH=;
$R^1$ is H;
Alk is —CH$_2$CH$_2$—;
Y is CH;
Z is CO; and
Ar is p-fluorophenyl.

17. A method according to claim 1, wherein the amount of said compound administered is about 1–100 mg per dose unit.

18. A method according to claim 1, wherein the amount of said compound administered is about 2–20 mg per dose unit.

19. A method according to claim 1, wherein the amount of said compound administered daily is about 0.02–2 mg/kg of body weight.

* * * * *